(12) United States Patent
Müller et al.

(10) Patent No.: US 6,194,417 B1
(45) Date of Patent: Feb. 27, 2001

(54) FUNGICIDE MIXTURES

(75) Inventors: Ruth Müller, Friedelsheim; Herbert Bayer; Hubert Sauter, both of Mannheim; Eberhard Ammermann, Heppenheim; Gisela Lorenz, Hambach; Siegfried Strathmann, Limburgerhof; Klaus Schelberger, Gönnheim; Dietrich Mappes, Westheim; Joachim Leyendecker, Ladenburg; Bernd Müller, Frankenthal, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/155,089
(22) PCT Filed: Apr. 22, 1997
(86) PCT No.: PCT/EP97/02021
§ 371 Date: Sep. 21, 1998
§ 102(e) Date: Sep. 21, 1998
(87) PCT Pub. No.: WO97/40675
PCT Pub. Date: Nov. 6, 1997

(30) Foreign Application Priority Data

Apr. 26, 1996 (DE) ............... 196 16 682
Apr. 30, 1996 (DE) ............... 196 17 235
Sep. 2, 1996 (DE) ............... 196 35 510

(51) Int. Cl.$^7$ ............... A01N 43/54; A01N 43/56
(52) U.S. Cl. ............... 514/256; 514/407
(58) Field of Search ............... 514/256, 407

(56) References Cited

FOREIGN PATENT DOCUMENTS 1 218 623   1/1971   (GB) .
9601256 *   1/1996   (WO) .

OTHER PUBLICATIONS

Pesticide Sci.,BD 44, N4. 1, May 1995, 77–79.
Research Disclosure No. 348 (1993).

\* cited by examiner

Primary Examiner—Allen J. Robinson
(74) Attorney, Agent, or Firm—Keil & Weinkauf

(57) ABSTRACT

Fungicidal mixtures, comprising
a) oxime ether of the formula I

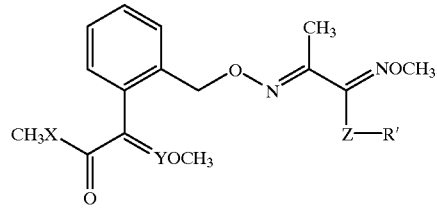

where the substituents have the following meanings:
X is oxygen or amino (NH);
Y is CH or N;
Z is oxygen, sulfur, amino (NH) or $C_1$–$C_4$-alkylamino (N—$C_1$–$C_4$-alkyl);
R' is $C_1$–$C_6$-alkyl, $C_1$–$C_6$-haloalkyl, $C_3$–$C_6$-alkenyl, $C_2$–$C_6$-haloalkenyl, $C_3$–$C_6$-alkynyl, $C_3$–$C_6$-haloalkynyl, $C_3$–$C_6$-cycloalkylmethyl, or is benzyl which can be partially or fully halogenated and/or can have attached to it one to three of the following radicals: cyano, $C_1$–$C_4$-alkyl, $C_1$–$C_4$-haloalkyl, $C_1$–$C_4$-alkoxy, $C_1$–$C_4$-halo-alkoxy and $C_1$–$C_4$-alkylthio; and/or
b) a carbamate of the formula I,

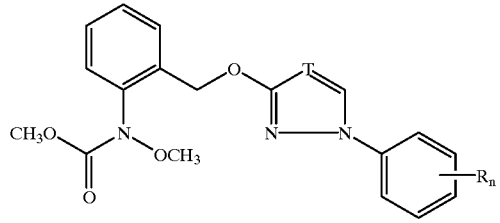

where T is CH or N, n is 0, 1 or 2 and R is halogen, $C_1$–$C_4$-alkyl or $C_1$–$C_4$-haloalkyl, it being possible for the radicals R to be different when n is 2, and
c) (±)-(2-chlorophenyl)(4-chlorophenyl)(pyrimidin-5-yl)methanol

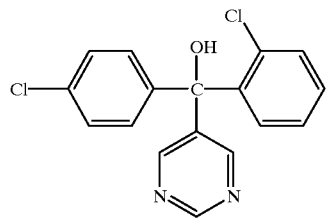

in a synergistically active amount.

5 Claims, No Drawings

FUNGICIDE MIXTURES

This application is a 371 of PCT/EP97/02021, filed Apr. 22, 1997

The present invention relates to a fungicidal mixture which comprises a) an oxime ether of the formula I

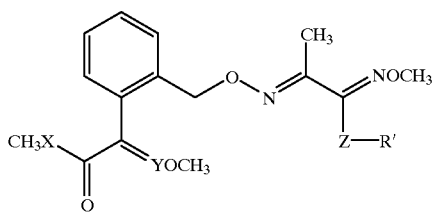

(I)

where the substituents have the following meanings:
X is oxygen or amino (NH);
Y is CH or N;
Z is oxygen, sulfur, amino (NH) or C+hd 1–C+hd 4-alkylamino (N-C+hd 1–C+hd 4-alkyl);
R' is C+hd 1–C+hd 6-alkyl, C+hd 1–C+hd 6-haloalkyl, C+hd 3–C+hd 6-alkenyl, C+hd 2–C+hd 6-haloalkenyl, C+hd 3–C+hd 6-alkynyl, C+hd 3–C+hd 6-haloalkynyl, C+hd 3–C+hd 6-cycloalkylmethyl, or is benzyl which can be partially or fully halogenated and/or can have attached to it one to three of the following radicals: cyano, C+hd 1–C+hd 4-alkyl, C+hd 1–C+hd 4-haloalkyl, C+hd 1–C+hd 4-alkoxy, C+hd 1–C+hd 4-haloalkoxy and C+hd 1–C+hd 4-alkylthio; +ps and/or b) a carbamate of the formula II

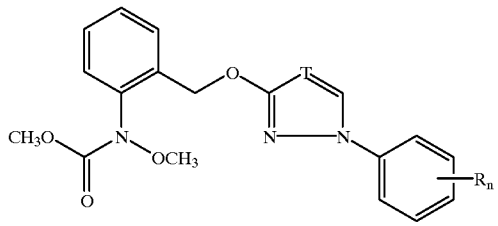

(II)

where T is CH or N, n is 0, 1 or 2 and R is halogen, C+hd 1–C+hd 4-alkyl or C+hd 1–C+hd 4-haloalkyl, it being possible for the radicals R to be different when n is 2, and c) (±)-(2-chlorophenyl)(4-chlorophenyl)(pyrimidin-5-yl) methanol III

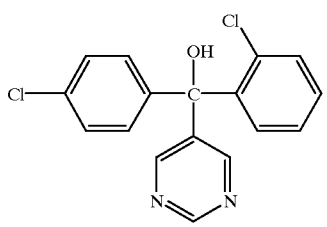

(III)

in asynergistically active amount.

Moreover, the invention relates to methods of controlling harmful fungi with mixtures of the compounds I and II and to the use of the compound I and the compound II for the preparation of such mixtures.

The compounds of the formula I, their preparation and their action against harmful fungi have been disclosed in the literature (WO-A 95/21,153, WO-A 95/21,154, DE-A 195 28 651.0).

Compounds of the formula II, their preparation and their action against harmful fungi have been described in WO-A 96/01,256 and WO-A 96/01,258.

The compound III (GB-A 1,218,623; common name: fenarimol), its preparation and its action against harmful fungi is also disclosed.

It was an object of the present invention to provide mixtures which have an improved activity gainst harmful fungi combined with a reduced total amount of active ingredients applied (synergistic mixtures) with a view to reducing the rates of application and to improving the spectrum of action of the known compounds.

Accordingly, we have found that this object is achieved by the mixture defined at the outset. Moreover, we have found that better control of the harmful fungi is possible by applying the compounds I and/or II and the compound III simultaneously together or separately or by applying the compounds I and/or II and the compound III in succession than when the individual compounds are used.

The invention covers binary mixtures of compounds I and III or II and III as well as mixtures of compounds I, II and III.

In particular, the general formula I represents oxime ethers in which X is oxygen and Y is CH or X is amino and Y is N.

Moreover, preferred compounds I are those where Z is oxygen.

Equally, preferred compounds I are those where R' is alkyl or benzyl.

Especially preferred with a view to their use in the synergistic mixtures according to the invention are the compounds I compiled in the tables which follow:

TABLE 1

Compounds of the formula IA where ZR' for each compound corresponds to one row of Table A

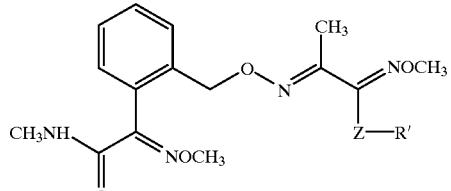

(IA)

TABLE 2

Compounds of the formula IB where ZR' for each compound corresponds to one row of Table A

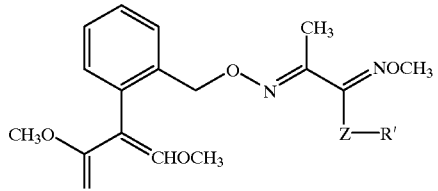

(IB)

TABLE A

| No. | ZR' |
|---|---|
| I.1 | O—CH$_2$CH$_2$CH$_3$ |
| I.2 | O—CH(CH$_3$)$_2$ |
| I.3 | O—CH$_2$CH$_2$CH$_2$CH$_3$ |
| I.4 | O—CH(CH$_3$)CH$_2$CH$_3$ |
| I.5 | O—CH$_2$CH(CH$_3$)$_2$ |
| I.6 | O—C(CH$_3$)$_3$ |
| I.7 | S—C(CH$_3$)$_3$ |
| I.8 | O—CH(CH$_3$)CH$_2$CH$_2$CH$_3$ |
| I.9 | O—CH$_2$C(CH$_3$)$_3$ |
| I.10 | O—CH$_2$C(Cl)=CCl$_2$ |
| I.11 | O—CH$_2$CH=CH—Cl (trans) |
| I.12 | O—CH$_2$C(CH$_3$)=CH$_2$ |
| I.13 | O—CH$_2$-(cyclopropyl) |
| I.14 | O—CH$_2$—C$_6$H$_5$ |
| I.15 | O—CH$_2$—[4-F—C$_6$H$_4$] |
| I.16 | O—CH$_2$CH$_3$ |
| I.17 | O—CH(CH$_2$CH$_3$)$_2$ |

In relation to the C=Y double bond, the compounds of the formula I can be in the E or the Z configuration (in relation to the carboxylic acid function). Accordingly, they can be used in the mixture according to the invention in each case either in the form of the pure E or z isomers or else in the form of an E/Z isomer mixture. The E/Z isomer mixture or the E isomer are preferably used in each case, the E isomer of the compound I being especially preferred.

The C=N double bonds of the oxime ether groups in the side chain of the compounds I can be in each case in the form of pure E or Z isomers or in the form of E/Z isomer mixtures. The compounds I can be used in the mixtures according to the invention as isomer mixtures or else as pure isomers. With a view to their use, compounds I which are particularly preferred are those where the terminal oxime ether group of the side chain is in the cis configuration (OCH$_3$ group in relation to ZR').

Due to the basic character, the compounds I, II and III are capable of forming adducts or salts with inorganic or organic acids or with metal ions.

In particular, the formula II represents carbamates in which the combination of the substituents corresponds to one row of the table which follows:

TABLE 3

| No. | T | R$_n$ |
|---|---|---|
| II.1 | N | 2-F |
| II.2 | N | 3-F |
| II.3 | N | 4-F |
| II.4 | N | 2-Cl |
| II.5 | N | 3-Cl |
| II.6 | N | 4-Cl |
| II.7 | N | 2-Br |
| II.8 | N | 3-Br |
| II.9 | N | 4-Br |
| II.10 | N | 2-CH$_3$ |
| II.11 | N | 3-CH$_3$ |
| II.12 | N | 4-CH$_3$ |
| II.13 | N | 2-CH$_2$CH$_3$ |
| II.14 | N | 3-CH$_2$CH$_3$ |
| II.15 | N | 4-CH$_2$CH$_3$ |
| II.16 | N | 2-CH(CH$_3$)$_2$ |
| II.17 | N | 3-CH(CH$_3$)$_2$ |
| II.18 | N | 4-CH(CH$_3$)$_2$ |
| II.19 | N | 2-CF$_3$ |
| II.20 | N | 3-CF$_3$ |
| II.21 | N | 4-CF$_3$ |
| II.22 | N | 2,4-F$_2$ |
| II.23 | N | 2,4-Cl$_2$ |
| II.24 | N | 3,4-Cl$_2$ |
| II.25 | N | 2-Cl, 4-CH$_3$ |
| II.26 | N | 3-Cl, 4-CH$_3$ |
| II.27 | CH | 2-F |
| II.28 | CH | 3-F |
| II.29 | CH | 4-F |
| II.30 | CH | 2-Cl |
| II.31 | CH | 3-Cl |
| II.32 | CH | 4-Cl |
| II.33 | CH | 2-Br |
| II.34 | CH | 3-Br |
| II.35 | CH | 4-Br |
| II.36 | CH | 2-CH$_3$ |
| II.37 | CH | 3-CH$_3$ |
| II.38 | CH | 4-CH$_3$ |
| II.39 | CH | 2-CH$_2$CH$_3$ |
| II.40 | CH | 3-CH$_2$CH$_3$ |
| II.41 | CH | 4-CH$_2$CH$_3$ |
| II.42 | CH | 2-CH(CH$_3$)$_2$ |
| II.43 | CH | 3-CH(CH$_3$)$_2$ |
| II.44 | CH | 4-CH(CH$_3$)$_2$ |
| II.45 | CH | 2-CF$_3$ |
| II.46 | CH | 3-CF$_3$ |
| II.47 | CH | 4-CF$_3$ |
| II.48 | CH | 2,4-F$_2$ |
| II.49 | CH | 2,4-Cl$_2$ |
| II.50 | CH | 3,4-Cl$_2$ |
| II.51 | CH | 2-Cl, 4-CH$_3$ |
| II.52 | CH | 3-Cl, 4-CH$_3$ |

The compounds II.12, II.23, II.32 and II.38 are especially preferred.

Examples of inorganic acids are hydrohalic acids such as hydrofluoric acid, hydrochloric acid, hydrobromic acid and hydroiodic acid, sulfuric acid, phosphoric acid and nitric acid.

Suitable organic acids are, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals having from 1 to 20 carbon atoms), arylsulfonic acids or -disulfonic acids (aromatic radicals such as phenyl and naphthyl which have attached to them one or two sulfo groups), alkylphosphonic acids (phosphonic acids having straight-chain or branched alkyl radicals of from 1 to 20 carbon atoms), arylphosphonic acids or -diphosphonic acids (aromatic radicals such as phenyl and naphthyl which have attached to them one or two phosphoric acid radicals), it being possible for the alkyl or aryl radicals to have attached to them further substituents, eg. p-toluenesulfonic acid, salicylic acid, p-aminosalicylic acid, 2-phenoxybenzoic acid, 2-acetoxybenzoic acid etc.

Suitable metal ions are, in particular, the ions of the elements of the second main group, in particular calcium and magnesium, and of the third and fourth main group, in particular aluminum, tin and lead, and of the first to eighth sub-group, in particular chromium, manganese, iron, cobalt, nickel, copper, zinc and others. Especially preferred are the metal ions of the elements of the sub-groups of the fourth period. The metals can in this case be in the various valences which they can assume.

When preparing the mixtures, it is preferred to employ the pure active ingredients I, II and III, with which further active ingredients against harmful fungi or other pests such as insects, arachnids or nematodes, or else herbicidal or growth-regulating active ingredients or fertilizers can be admixed, if so desired.

The mixtures of the compounds I and/or II and III, or the simultaneous joint or separate use of the compounds I and/or II and III, are distinguished by an outstanding activity against a broad spectrum of phytopathogenic fungi, in particular from the classes of the Ascomycetes, Deuteromycetes, Phycomycetes and Basidiomycetes. Some of them act systemically and can therefore be employed as foliar- and soil-acting fungicides.

They are especially important for controlling a large number of fungi in a variety of crop plants such as cotton, vegetable species (eg. cucumbers, beans and curcubits), barley, grass, oats, coffee, maize, fruit species, rice, rye, soybeans, grapevine, wheat, ornamentals, sugar cane, and a variety of seeds.

They are particularly suitable for controlling the following phytopathogenic fungi: *Erysiphe graminis* (powdery mildew) on cereals, *Erysiphe cichoracearum* and *Sphaerotheca fuliginea* on curcubits, *Podosphaera leucotricha* on apples, *Uncinula necator* on grapevines, Puccinia species on cereals, Rhizoctonia species on cotton, rice and lawn, Ustilago species on cereals and sugar cane, venturia inaequalis (scab) on apples, Helminthosporium species on cereals, *Rhynchosporium secalis, Septoria nodorum* on wheat, *Botrytis cinera* (gray mold) on strawberries, vegetables, ornamentals and grapevines, *Cercospora arachidicola* on peanuts, *Pseudocercosporella herpotrichoides* on wheat and barley, *Pyricularia oryzae* on rice, *Phytophthora infestans* on potatoes and tomatoes, *Plasmopara viticola* on grapevines, Alternaria species on vegetables and fruit, and Fusarium and Verticillium species.

Furthermore, they can be used in the protection of materials (eg. in the protection of wood), for example against *Paecilomyces variotii.*

The compounds I and/or II and III can be applied simultaneously together or separately or in succession, the sequence, in the case of separate application, generally not having any effect on the result of the control measures.

The compounds I and/or II and III are normally used in a weight ratio of from 10:1 to 0.1:1, preferably 5:1 to 0.2:1, in particular 3:1 to 0.3:1.

The application rates of the mixtures according to the invention are from 0.01 to 3 kg/ha, preferably 0.01 to 1.5 kg/ha, in particular 0.01 to 0.5 kg/ha, depending on the nature of the desired effect.

In the case of the compounds I and/or II, the application rates are in general from 0.005 to 0.5 kg/ha, preferably 0.005 to 0.5 kg/ha, in particular 0.005 to 0.3 kg/ha.

Correspondingly, in the case of the compound III, the application rates are normally from 0.005 to 0.5 kg/ha, preferably 0.01 to 0.5 kg/ha, in particular 0.01 to 0.3 kg/ha.

For seed treatment, the application rates of the mixture are generally from 0.001 to 10 g/kg seed, preferably 0.01 to 10 g/kg, in particular 0.01 to 8 g/kg.

If phytopathogenic harmful fungi are to be controlled, the separate or joint application of the compounds I and/or and III or of the mixtures of the compounds I and/or II and III is effected by spraying or dusting the seeds, the plants or the soils before or after sowing of the plants, or before or after plant emergence.

The fungicidal synergistic mixtures according to the invention, or the compounds I and/or II and III, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guarantee as fine and uniform as possible a distribution of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, of alkyl- and alkylarylsulfonates, of alkyl, lauryl ether and fatty alcohol sulfates, and salts of sulfated hexa-, hepta- and octadecanols or fatty alcohol glycol ethers, condensates of sulfonated naphthalene and its derivatives with formaldehyde, condensates of naphthalene, or of the naphthalenesulfonic acids, with phenol and formaldehyde, polyoxyethylene octylphenol ether, ethoxylated isooctyl-, octyl- or nonylphenol, alkylphenol polyglycol ethers or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, ligninsulfite waste liquors or methylcellulose.

Powders, materials for spreading and dusts can be prepared by mixing or jointly grinding the compounds I and/or II or III or the mixture of the compounds I and/or II and III with a solid carrier.

Granules (eg. coated granules, impregnated granules or homogeneous granules) are normally prepared by binding the active ingredient, or active ingredients, to a solid carrier.

Fillers or solid carriers are, for example, mineral earths such as silica gel, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, and fertilizers such as ammonium sulfate, ammonium phosphate, ammonium nitrate,ureas, and products of vegetable origin such as cereal meal, tree bark meal, wood meal and nutshell meal, cellulose powders or other solid carriers.

The formulations generally comprise from 0.1 to 95% by weight, preferably 0.5 to 90% by weight, of one of the compounds I and/or II or III, or of the mixture of the compounds I and/or II and III. The active ingredients are employed in a purity of from 90% to 100%, preferably 95% to 100% (according to NMR or HPLC spectrum).

The compounds I and/or II and III, or the mixtures, or the corresponding formulations, are applied by treating the harmful fungi or the plants, seeds, soils, areas, materials or spaces to be kept free from them with a fungicidally active amount of the mixture, or of the compounds I and/or II and III in the case of separate application. Application can be effected before or after infection by the harmful fungi.

The fungicidal activity of the compounds and of the mixtures is demonstrated by the following experiments:

The active ingredients, separately or together, are formulated as a 10% emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Emulphor® EL (Emulan® EL, emulsifier based on ethoxylated fatty alcohols) and diluted with water to give the desired concentration.

Evaluation is carried out by determining the infected leaf areas in percent. These percentages are converted into efficacies. The expected efficacies of the mixtures of the active ingredients are determined using Colby's formula [R. S. Colby, Weeds 15, 20–22 (1967)] and compared with the observed efficacies. Colby's formula:

$$E = x + y - x \cdot y / 100$$

E expected efficacy, expressed in % of the untreated control, when using the mixture of the active ingredients A and B at concentrations of a and b x efficacy, expressed in % of the untreated control, when using active ingredient A at a concentration of a y efficacy, expressed in % of the untreated control, when using active ingredient B at a concentration of b The efficacy (W) is calculated as follows using Abbot's formula:

$$W=(1-\alpha)\cdot 100/\beta$$

α is the fungal infection of the treated plants in % and
β is the fungal infection of the untreated (control) plants in %

An efficacy of 0 means that the infection level of the treated plants corresponds to that of the untreated control plants; an efficacy of 100 means that the treated plants are not infected.

Examples 1–7—curative action against *Puccinia recondita* (leaf rust of wheat) in wheat Leaves of potted wheat seedlings of the variety "Frühgold" were dusted with leaf rust (*Puccinia recondita*) spores. The pots were then kept in a chamber of high atmospheric humidity (90 to 95%) at 20 to 22° C. for 24 hours. During this time, the spores germinated and the germ tubes penetrated into the leaf tissue. The next day, the infected plants were sprayed to run-off point with an aqueous active compound preparation prepared from a stock solution of 10% of active compound, 63% of cyclohexanone and 27% of emulsifier. After the spray coating had dried on, the test plants were cultivated in the greenhouse at 20–22° C. and 65–70% of relative atmospheric humidity for 7 days. The extent of the fungal development on the leaves was then determined.

The visually determined percentages of infested leaf area were converted into efficacies in% of the untreated control. An efficacy of 0 means that the degree of infestation is the same as in the untreated control, an efficacy of 100 is equivalent to 0% infestation. The expected efficacies for active compound combinations were calculated using the Colby formula (Colby, S. R. "Calculating synergistic and antagonistic responses of herbicide combinations", Weeds 15, pages 20 to 22, 1967) and compared with the observed efficacies.

TABLE 4

| Ex. | Active compound | Active compound concentration in the spray liquor in ppm | Efficacy in % of the untreated control |
|---|---|---|---|
| 1v | control (untreated) | (100% infestation) | 0 |
| 2v | A = Tab. 1A, No. 2 | 6.3 | 30 |
|   |   | 3.1 | 0 |
| 3v | B = Tab. 1A, No. 4 | 3.1 | 10 |
| 4v | III = fenarimol | 6.3 | 70 |
|   |   | 3.1 | 0 |

TABLE 5

| Ex. | Active compound concentration in the spray liquor in ppm | Observed efficacy | Calculated efficacy*) |
|---|---|---|---|
| 5 | 6.3 A + 3.1 III | 90 | 79 |
| 6 | 3.1 A + 3.1 III | 40 | 0 |
| 7 | 3.1 B + 3.1 III | 50 | 10 |

*calculated using the Colby formula

Examples 8–15 -action against *Puccinia recondita* (leaf rust of wheat) in wheat Leaves of potted wheat seedlings of the variety "Frühgold" were dusted with leaf rust (*Puccinia recondita*) spores. The pots were then kept in a chamber of high atmospheric humidity (90 to 95%) at 20 to 22° C. for 24 hours. During this time, the spores germinated and the germ tubes penetrated into the leaf tissue. The next day, the infected plants were sprayed to run-off point with an aqueous active compound preparation prepared from a stock solution of 10% of active compound, 63% of cyclohexanone and 27% of emulsifier. After the spray coating had dried on, the test plants were cultivated in the greenhouse at 20–22° C. and 65–70% of relative atmospheric humidity for 7 days. The extent of the fungal development on the leaves was then determined.

The visually determined percentages of infested leaf area were converted into efficacies in% of the untreated control. An efficacy of 0 means that the degree of infestation is the same as in the untreated control, an efficacy of 100 is equivalent to 0% infestation. The expected efficacies for active compound combinations were calculated using the Colby formula (Colby, S. R. "Calculating synergistic and antagonistic responses of herbicide combinations", Weeds 15, pages 20 to 22, 1967) and compared with the observed efficacies.

TABLE 6

| Ex. | Active compound | Active compound concentration in the spray liquor in ppm | Efficacy in % |
|---|---|---|---|
| 8v. | control (untreated) | (90% infestation) | 0 |
| 9v | compound No. II.32 from Table 3 = C | 3.1 1.6 | 0 |
| 10v | compound No. II.38 from Table 3 = D | 3.1 1.6 | 70 0 |
| 11v | III = fenarimol | 12.5 6.3 | 20 0 |

TABLE 7

| Ex. | Active compound concentration in the spray liquor in ppm | Observed efficacy | Calculated efficacy |
|---|---|---|---|
| 12 | 3.1 C + 12.5 III | 40 | 20 |
| 13 | 1.6 C + 6.3 III | 25 | 0 |
| 14 | 3.1 D + 12.5 III | 90 | 76 |
| 15 | 1.6 D + 6.3 III | 30 | 0 |

We claim:

1. A fungicidal mixture comprising
   a) a carbamate of the formula II,

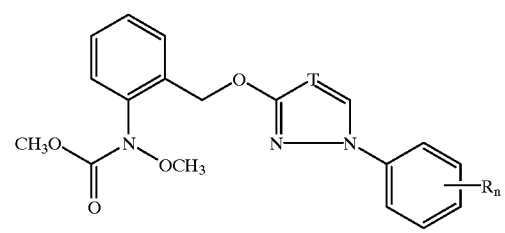

(II)

where T is CH, n is 0, 1 or 2 and R is independently selected from the group consisting of halogen, $C_1$–$C_4$-alkyl or $C_1$–$C_4$-haloalkyl, and
   b) (±)-(2-chlorophenyl)(4-chlorophenyl)(pyrimidin-5-yl)-methanol III

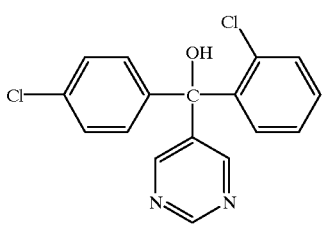

(III)

in a synergistically effective amount wherein the weight ratio of the carbamate II to the compound III is 10:1 to 0.1:1.

2. A method of controlling harmful fungi, which comprises treating the harmful fungi, their environment, or the plants, seeds, soils, areas, materials or spaces to be kept free from them with a compound of the formula II as set forth in claim 1 and the compound of the formula III as set forth in claim 1 in a synergistically effective amount.

3. A method as claimed in claim 2, wherein compound II and compound III are applied simultaneously together or separately or in succession.

4. A method as claimed in claim 2, wherein the harmful fungi, their environment, or the plants, seeds, soils, areas, materials or spaces to be kept free from them are treated with from 0.005 to 0.5 kg/ha of a compound II.

5. A method as claimed in claim 2, wherein the harmful fungi, their environment, or the plants, seeds, soils, areas, materials or spaces to be kept free from them are treated with from 0.05 to 0.5 kg/ha of the compound III.

* * * * *